US012789169B2

(12) United States Patent
Pollefeyt et al.

(10) Patent No.: US 12,789,169 B2
(45) **Date of Patent: *Nov. 10, 2026**

(54) CATALYST AND PROCESS FOR THE DEHYDROGENATION OF ALKANES TO OLEFINS

(71) Applicant: Dow Global Technologies LLC, Midland, MI (US)

(72) Inventors: Glenn Pollefeyt, Wondelgem (BE); Kevin Blann, Missouri City, TX (US); Daniela Ferrari, Rosharon, TX (US); Alexey Kirilin, Terneuzen (NL); Adam Chojecki, East Flanders (BE); Cheng L. Chung, Houston, TX (US); Andrzej Malek, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 138 days.

This patent is subject to a terminal disclaimer.

(21) Appl. No.: 18/683,045

(22) PCT Filed: Aug. 17, 2022

(86) PCT No.: PCT/US2022/075074

§ 371 (c)(1),
(2) Date: Feb. 12, 2024

(87) PCT Pub. No.: WO2023/028434

PCT Pub. Date: Mar. 2, 2023

(65) Prior Publication Data

US 2024/0351004 A1 Oct. 24, 2024

Related U.S. Application Data

(60) Provisional application No. 63/235,996, filed on Aug. 23, 2021.

(51) Int. Cl.

| | |
|---|---|
| ***B01J 23/31*** | (2006.01) |
| ***B01J 23/00*** | (2006.01) |
| ***B01J 37/00*** | (2006.01) |
| ***B01J 37/04*** | (2006.01) |
| ***B01J 37/10*** | (2006.01) |
| ***C07C 5/32*** | (2006.01) |

(52) U.S. Cl.

CPC ............. *B01J 23/31* (2013.01); *B01J 23/002* (2013.01); *B01J 37/0018* (2013.01); *B01J 37/0036* (2013.01); *B01J 37/009* (2013.01); *B01J 37/04* (2013.01); *B01J 37/10* (2013.01); *C07C 5/322* (2013.01); *B01J 2523/54* (2013.01); *B01J 2523/55* (2013.01); *B01J 2523/56* (2013.01); *B01J 2523/68* (2013.01); *C07C 2523/20* (2013.01); *C07C 2523/22* (2013.01); *C07C 2523/31* (2013.01)

(58) Field of Classification Search

CPC ...... B01J 23/31; B01J 23/002; B01J 37/0018; B01J 37/0036; B01J 37/009; B01J 37/04; B01J 37/10; B01J 2523/54; B01J 2523/55; B01J 2523/56; B01J 2523/68; C07C 5/322; C07C 2523/20; C07C 2523/22; C07C 2523/31

See application file for complete search history.

(56) References Cited

U.S. PATENT DOCUMENTS

| | | | | |
|---|---|---|---|---|
| 4,250,346 | A | 2/1981 | Young et al. | |
| 4,524,236 | A | 6/1985 | McCain | |
| 9,156,764 | B2 | 10/2015 | Han et al. | |
| 9,409,156 | B2 | 8/2016 | Sanchez Valente et al. | |
| 10,406,517 | B2 * | 9/2019 | Simanzhenkov ...... | B01J 37/009 |
| 2004/0147393 | A1 | 7/2004 | Hibst et al. | |
| 2005/0176985 | A1 | 8/2005 | Bogan, Jr. et al. | |
| 2006/0258529 | A1 | 11/2006 | Diefenbacher et al. | |
| 2009/0042723 | A1 * | 2/2009 | Wang ...................... | C07C 57/04 502/312 |
| 2010/0255986 | A1 | 10/2010 | Gaffney et al. | |
| 2011/0245571 | A1 | 10/2011 | Kustov et al. | |
| 2014/0114109 | A1 * | 4/2014 | Sanchez Valente ...... | C07C 5/48 585/658 |
| 2017/0233312 | A1 | 8/2017 | Hossain et al. | |
| 2017/0252728 | A1 * | 9/2017 | De Rooij ............... | B01J 37/031 |
| 2024/0352341 | A1 * | 10/2024 | Ferrari ..................... | B01J 23/28 |

FOREIGN PATENT DOCUMENTS

| | | | |
|---|---|---|---|
| CA | 2859935 | A1 | 2/2016 |
| DE | 4423975 | A1 | 1/1996 |
| DE | 19545095 | A1 | 6/1997 |
| EP | 2179790 | A1 | 4/2010 |
| JP | H08198782 | A | 8/1996 |
| RU | 2393144 | C1 | 6/2010 |
| RU | 2612305 | C1 | 3/2017 |
| WO | 2005120702 | A1 | 12/2005 |
| WO | 2016059518 | A1 | 4/2016 |
| WO | 2018141562 | A1 | 8/2018 |
| WO | 2018141653 | A1 | 8/2018 |
| WO | 2018141654 | A1 | 8/2018 |
| WO | 2018232133 | A1 | 12/2018 |

OTHER PUBLICATIONS

Kuwait Examination Report dated May 1, 2025, pertaining to KW Patent Application No. KW/P/2024/001124, 4 pgs.

International Search Report and Written Opinion dated Dec. 12, 2022, pertaining to Int'l Patent Application No. PCT/US2022/075067, 12 pgs.

International Search Report and Written Opinion dated Dec. 13, 2022, pertaining to Int'l Patent Application No. PCT/US2022/075074, 13 pgs.

Bakare et al. "Fluidized bed ODH of ethane to ethylene over VOx—Mo0x/Y—Al2O3 catalyst: Desorption kinetics and catalytic activity", Chemical Engineering Journal 278 (2015) 207-216.

(Continued)

*Primary Examiner* — Ellen M Mcavoy

(74) *Attorney, Agent, or Firm* — Dinsmore & Shohl LLP

(57) ABSTRACT

An oxidative dehydrogenation catalyst having: a structure having a formula $Mo_vV_wNb_yBi_zO_x$, where v is 1, w is from 0.1 to 0.5, y is from 0.001 to 0.3, z is from 0.01 to 0.3, and x is the oxygen content required to charge-balance the structure. The oxidative dehydrogenation catalyst has a Pba2-32 space group, characterized by reflections determined with Cu—$K_\alpha$ X-ray diffraction (XRD) as follows.

15 Claims, No Drawings

(56) References Cited

OTHER PUBLICATIONS

Melzer et al. "Design and synthesis of highly active MoVTeNb-oxides for ethane oxidative dehydrogenation", Nature Communications (2019) 10:4012, https://doi.org/10.1038/s41467-019-11940-0, www.nature.com/naturecommunications, 9 pgs.
US Non-Final Office Action dated Oct. 2, 2025, pertaining to U.S. Appl. No. 18/683,043, 18 pgs.
Hibst et al., "New Cs-containing Mo—V4+ based oxides with the structure of the M1 phase-Base for new catalysts for the direct alkane activation", Catalysis Today 117 (2006) 234-241.
Ishikawa et al., "Synthesis of Crystalline Microporous Mo—V—Bi Oxide for Selective (Amm)Oxidation of Light Alkanes", Chem. Mater. 2017, 29, 2939-2950.
Valente et al., "Oxidative Dehydrogenation of Light Alkanes", The Catalyst Review (SSN 0898-3089), Aug. 2018, vol. 31, No. 8., 11 pgs.
Svintsitskiy et al., "NAP-XPS and in situ XRD study of the stability of Bi-modified MoVnbTeO catalysts for oxidative dehydrogenation of ethane", Applied Catalysis A, General 579 (2019) 141-150.
Thorsteinson et al., "The Oxidative Dehydrogenation of Ethane over Catalysts Containing Mixed Oxides of Molybdenum and Vanadium", Journal of Catalysis 52, 116-132 (1978).
Al-Ghamdi et al., "VOx/c—Al2O3 catalyst for oxidative dehydrogenation of ethane to ethylene: Desorption kinetics and catalytic activity", Applied Catalysis A: General 450 (2013) 120-130.
Kuwait Examination Report dated Dec. 5, 2025, pertaining to KW Patent Application No. KW/P/2024/001278, 6 pgs.
Russian Office Action dated Jan. 29, 2026, pertaining to RU Patent Application No. 2024106434, 12 pgs.
Saudi Arabian Examination Report dated Jan. 10, 2026, pertaining to SA Patent Application No. 1120240647, 7 pgs.
Singapore Search Report dated Feb. 11, 2026, pertaining to SG Patent Application No. 11202400899R, 8 pgs.
Singapore Search Report dated Feb. 11, 2026, pertaining to SG Patent Application No. 11202400905Y, 9 pgs.
Saudi Arabian Examination Report dated Mar. 25, 2026, pertaining to SA Patent Application No. 1120240648, 4 pgs.
Chinese Office Action dated Jun. 27, 2026, pertaining to CN Patent Application No. 202280054417.9, 20 pgs.
US Final Office Action dated Jun. 1, 2026, pertaining to U.S. Appl. No. 18/683,043, 18 pgs.
Brazilian Technical Report dated Jul. 31, 2026, pertaining to BR Patent Application No. BR112024002549-7, 8 pgs.
Japanese Notice of Reasons for Refusal dated Jun. 23, 2026, pertaining to JP Patent Application No. 2024-508952, 16 pgs.
Japanese Notice of Reasons for Refusal dated Jul. 9, 2026, pertaining to JP Patent Application No. 2024-509475, 7 pgs.
Saudi Arabian Examination Report dated Aug. 14, 2026, pertaining to SA Patent Application No. 1120240648.2, 9 pgs.

* cited by examiner

CATALYST AND PROCESS FOR THE DEHYDROGENATION OF ALKANES TO OLEFINS

CROSS-REFERENCE TO RELATED APPLICATIONS

The present application is a National Phase Entry under 35 U.S.C. § 371 of International Patent Application No. PCT/US2022/075074 filed Aug. 17, 2022, which claims priority to U.S. Provisional Patent Application No. 63/235,996, filed Aug. 23, 2021, and entitled "CATALYST AND PROCESS FOR THE DEHYDROGENATION OF ALKANES TO OLEFINS," the entirety of which is incorporated by reference herein.

BACKGROUND

Field

The present specification generally relates to catalysts for the dehydrogenation of alkanes to olefins, such as catalysts for converting ethane to ethylene.

Technical Background

Conventional catalysts for converting alkanes to olefins, such as converting ethane to ethylene and acetic acid, are based on molybdenum (Mo), vanadium (V), and niobium (Nb) and include promoters such as calcium (Ca), sodium (Na), antimony (Sb), or tellurium (Te). In particular, Te is a common promoter included in the conventional catalysts. Processes using such catalysts require an oxygen co-feed and utilize an oxidative dehydrogenation process at low temperature, such as below 500° C., and low pressures, such as below 300 pounds per square inch gauge (psig) (or about 20 barg).

SUMMARY

According to one embodiment, an oxidative dehydrogenation catalyst comprises: a structure comprising oxides of molybdenum (Mo), vanadium (V), niobium (Nb), and bismuth (Bi) having a formula $Mo_vV_wNb_yBi_zO_x$, wherein v is 1, w is from 0.1 to 0.5, y is from 0.001 to 0.3, z is from 0.01 to 0.3, and x is the oxygen content required to charge-balance the structure, the oxidative dehydrogenation catalyst has a crystalline structure with the Pba2-32 space group, characterized by reflections determined with Cu—$K_\alpha$ X-ray diffraction (XRD) as follows:

| 2θ (±0.3°) | Rel. Intensity (%) |
|---|---|
| 5.3 | 0.2-8 |
| 6.6 | 1.5-15 |
| 7.84 | 2.5-45 |
| 8.95 | 4-21 |
| 22.17 | 100 |
| 27.2 | 20-50 |
| 28.1 | 10-30 |

According to another embodiment, a method for forming an oxidative dehydrogenation catalyst comprises: adding a molybdenum-containing compound, a vanadium-containing compound, a bismuth-containing compound, a niobium-containing compound, and one or more organic acids to a

2 mixture of complexing agents and water; synthesizing $Mo_vV_wNb_yBi_zO_x$ by hydrothermal synthesis at a hydrothermal synthesis temperature for a period of time, where v is 1, w is from 0.1 to 0.5, y is from 0.001 to 0.3, z is from 0.01 to 0.3, and x is the oxygen content required to charge-balance the structure; and separating the $Mo_vV_wNb_yBi_zO_x$ from retained liquids.

In another embodiment, a method for converting paraffins to olefins comprises: contacting a feed stream comprising paraffins with the oxidative dehydrogenation catalyst; converting at least a portion of the paraffins to olefins, thereby yielding a product stream comprising paraffins and olefins; and separating the olefins from the paraffins in the product stream, wherein the oxidative dehydrogenation catalyst comprises: a structure comprising oxides of molybdenum (Mo), vanadium (V), niobium (Nb), and bismuth (Bi) having a formula $Mo_vV_wNb_yBi_zO_x$, wherein v is 1, w is from 0.1 to 0.5, y is from 0.001 to 0.3, z is from 0.01 to 0.3, and x is the oxygen content required to charge-balance the structure, the oxidative dehydrogenation catalyst has a Pba2-32 space group, characterized by reflections determined with Cu—$K_\alpha$ X-ray diffraction (XRD) as follows:

| 2θ (±0.3°) | Rel. Intensity (%) |
|---|---|
| 5.3 | 0.2-8 |
| 6.6 | 1.5-15 |
| 7.84 | 2.5-45 |
| 8.95 | 4-21 |
| 22.17 | 100 |
| 27.2 | 20-50 |
| 28.1 | 10-30 |

As would be recognized by one of ordinary skill in the art, the relative intensity may be affected by the preferential orientation effect and the above-disclosed relative intensities take into account such effects.

Additional features and advantages will be set forth in the detailed description that follows, and in part will be readily apparent to those skilled in the art from that description or recognized by practicing the embodiments described herein, including the detailed description which follows and the claims.

It is to be understood that both the foregoing general description and the following detailed description describe various embodiments and are intended to provide an overview or framework for understanding the nature and character of the claimed subject matter.

DETAILED DESCRIPTION

Reference will now be made in detail to embodiments of catalysts for the dehydrogenation of alkanes to olefins, such as catalysts for converting ethane to ethylene and methods for making such catalysts.

One issue with conventional oxidative dehydrogenation processes is that they require a co-feed stream of oxygen ($O_2$). This adds costs to the process by requiring equipment that can produce pure, or nearly pure, oxygen to use in the process. In addition, the presence of oxygen in the process increases the chances for undesired, dangerous combustion as the oxygen and hydrocarbons mix. Conventional catalysts also require a certain amount of oxygen to be present for the catalyst to remain stable. Finally, because of the nature of the catalyst, and the oxygen requirement for dehydrogenation of alkanes, conventional oxidative dehydrogenation processes for converting alkanes to olefins are conducted in fixed bed reactors, which requires down time to remove and replace or regenerate the catalyst. Accordingly, there is a need for improved catalysts that can convert alkanes to olefins. While, conventional catalysts may be used in oxidative dehydrogenation, they show limited stability when operated in a cyclic redox mode or in conditions with low partial pressure of $O_2$, typically encountered at the bottom sections of fixed bed reactors, because of the chemical changes, reduction and loss of elements like tellurium.

It has unexpectedly been found that compositional modifications of the conventional oxidative dehydrogenation catalysts, as disclosed and described herein, allow for stable reduction and oxidation (redox) cycling of the materials. Catalysts disclosed and described herein have oxygen carrying capacity that is high enough so that selective conversion of ethane to ethylene is obtained in a circulating reactor fed with oxygenated solids. By using catalysts disclosed and described herein, circulation rates that are industrially viable in circulating reactors may be used and adequate conversion and selectivity of ethane to ethylene is achieved. This eliminates the need for feeding oxygen to the reactor. Moreover, air can be used to reoxidize the spent catalyst. In addition, the reactor/regenerator system in use for the ethane conversion is exothermic and, thus, can be operated without additional heat input.

One currently used oxidative dehydrogenation catalyst comprises $MoVNbTeO_x$. Without being bound to any particular theory, it is believed that the crystal phase structure, or a similar crystal phase structure, of the $MoVNbTeO_x$, e.g. the Pba2-32 space group provides a structure that makes it possible to render a high yield of desired olefins. However, using this catalyst in an oxidative dehydrogenation process leads to significant catalyst stability concerns because Te is volatile under reducing conditions, causing reactor contamination with Te as well as potential collapse of the preferred crystalline structure of the catalyst. This will subsequently lead to activity/selectivity loss during the alkane to olefin conversion.

In embodiments disclosed and described herein, Te can be completely replaced in the $MoVNbTeO_x$ catalyst composition with bismuth (Bi), and using a specific hydrothermal synthesis method, which is disclosed in more detail herein, allows the catalyst to have a crystal structure that is similar to $MoVNbTeO_x$ such that the alkane to olefin conversion provides desired olefins. Accordingly, an oxidative dehydrogenation catalyst according to embodiments has a structure comprising molybdenum (Mo), vanadium (V), niobium (Nb) and bismuth (Bi). The oxidative dehydrogenation catalyst has a Pba2-32 space group crystal structure. The volatile Te is replaced with Bi, which allows for improved material stability over the known $MoVNbTeO_x$ catalysts while providing similar alkane conversion. For instance, in embodiments the oxidative dehydrogenation catalyst disclosed and described herein is both active (greater than 10% Ethane conversion), selective (greater than 65% ethylene selectivity), and renders stable performance under cyclic redox reaction conditions.

In one or more embodiments, the oxidative dehydrogenation catalyst has the following chemical formula: $Mo_vV_wNb_yBi_zO_x$, where v is 1.0 (e.g., Mo is used as the basis for the atomic ratios), w is from 0.1 to 0.5, y is from 0.001 to 0.3, z is from 0.01 to 0.3, and x is the oxygen content required to charge-balance the structure. In embodiments, w is from 0.2 to 0.5, from 0.3 to 0.5, from 0.4 to 0.5, from 0.1 to 0.4, from 0.2 to 0.4, from 0.3 to 0.4, from 0.1 to 0.3, from 0.2 to 0.3, or from 0.1 to 0.2. In embodiments, y is from 0.01 to 0.3, from 0.05 to 0.3, from 0.1 to 0.3, from 0.15 to 0.3, from 0.2 to 0.3, from 0.25 to 0.3, from 0.001 to 0.25, from 0.01 to 0.25, from 0.05 to 0.25, from 0.1 to 0.25, from 0.15 to 0.25, from 0.2 to 0.25, from 0.01 to 0.2, from 0.05 to 0.2, from 0.1 to 0.2, from 0.15 to 0.2, from 0.01 to 0.15, from 0.05 to 0.15, from 0.1 to 0.15, from 0.01 to 0.1, from 0.05 to 0.1, or from 0.01 to 0.05. In embodiments, z is from 0.05 to 0.3, from 0.10 to 0.3, from 0.15 to 0.3, from 0.2 to 0.3, from 0.25 to 0.3, from 0.01 to 0.25, is from 0.05 to 0.25, from 0.10 to 0.25, from 0.15 to 0.25, from 0.2 to 0.25, from 0.01 to 0.2, is from 0.05 to 0.2, from 0.10 to 0.2, from 0.15 to 0.2, from 0.01 to 0.15, is from 0.05 to 0.15, from 0.10 to 0.15, from 0.01 to 0.1, is from 0.05 to 0.1, or from 0.01 to 0.05. In embodiments, the oxidative dehydrogenation catalyst has the following formula: $MoV_{0.3}Nb_{0.1}Bi_{0.1}O_x$, where x is the oxygen content required to charge-balance the structure. It should be understood that embodiments of the $Mo_vV_wNb_yBi_zO_x$ catalyst having a Pba2-32 space that is essentially free of Te, such as having a Te/Mo atomic ratio that is less than or equal to 0.01.

It has been found that the presence of Nb in the oxidative dehydrogenation catalyst having the structure $Mo_vV_wNb_yBi_zO_x$ and a Pba2-32 space group crystal structure improves catalyst activity and selectivity in a lattice oxidative dehydrogenation process (which is where oxygen for the conversion is extracted from the lattice of the catalyst rather than through a molecular oxygen feed stream). Accordingly, in embodiments, the oxidative dehydrogenation catalyst consists of a structure comprising oxides of Mo, V, Nb, and Bi having the formula $Mo_vV_wNb_yBi_zO_x$ and a Pba2-32 space group crystal structure.

The crystal structure of the oxidative dehydrogenation catalyst disclosed and described herein can, in embodiments, also be measured using X-Ray Diffraction (XRD). For instance, and as would be understood by a skilled artisan, the position and relative intensity of XRD peaks at various 2θ angles can be used to describe the crystal structure of the oxidative dehydrogenation catalyst. In embodiments, the oxidative dehydrogenation catalyst has reflections determined with Cu—$K_\alpha$ XRD as shown in Table 1. In Table 1 below, the relative intensity (Rel. Intensity) of the diffractogram features is the largest at 2θ=22.17° and, thus, this relative intensity is set to 100% and used as the basis for the remaining relative intensities shown in Table 1. As would be recognized by one of ordinary skill in the art, the relative intensity may be affected by the preferential orientation effect and the above-disclosed relative intensities take into account such effects.

TABLE 1

| 2θ (±0.3°) | Rel. Intensity (%) |
|---|---|
| 5.3 | 0.2-8 |
| 6.6 | 1.5-15 |
| 7.84 | 2.5-45 |
| 8.95 | 4-21 |
| 22.17 | 100 |
| 27.2 | 20-50 |
| 28.1 | 10-30 |

As mentioned above, using a specific hydrothermal method for forming the oxidative dehydrogenation catalyst allows the oxidative dehydrogenation catalysts to be formed having the desired Pba2-32 crystal structure. Embodiments of these hydrothermal methods for forming the oxidative dehydrogenation catalyst will now be described in more detail.

Oxidative dehydrogenation catalysts having a $Mo_vV_wNb_yBi_zO_x$ structure are, in one or more embodiments, formed through a synthetic process started by adding a molybdenum-containing compound, a vanadium-containing compound, a bismuth-containing compound, a niobium-containing compound, and one or more organic acids to a mixture of alkylene glycol or alcohol amines and water to form a reaction mixture. In embodiments, the metal precursors are chosen as such that the precursors can be dissolved/digested under hydrothermal reaction conditions. $Mo_vV_wNb_yBi_zO_x$ is then synthesized from the reaction mixture by hydrothermal synthesis at a hydrothermal synthesis temperature for a period of time. After the period of time has passed, $Mo_vV_wNb_yBi_zO_x$ is separated from retained liquids. In one or more embodiments, the molybdenum-containing, vanadium-containing, bismuth-containing, niobium-containing compound, and one or more acids are added to the mixture of alkylene glycol and water sequentially.

In embodiments, the bismuth-containing compound is selected from the group consisting of bismuth oxide ($Bi_2O_3$), bismuth sulfate ($Bi_2(SO_4)_3$), bismuth citrate ($BiC_6H_5O_7$), and bismuth nitrate ($Bi(NO_3)_3$). In embodiments, the niobium-containing compound is selected from the group consisting of niobium oxide, niobic acid ($Nb_2O_5 \cdot nH_2O$), niobium ethoxide, and ammonium niobium oxalate and water ($(NH_4)Nb(C_2O_4)_2 \cdot nH_2O$). In embodiments, the molybdenum-containing compound can be ammonium heptamolybdate $(NH_4)_6Mo_7O_{24}$ or molybdenum trioxide ($MoO_3$), and the vanadium-containing compound can be ammonium metavanadate ($NH_4VO_3$), vanadyl sulfate ($VOSO_4$), or vanadium pentoxide ($V_2O_5$). The molybdenum-containing compound and the vanadium-containing compound are, in embodiments, $MoO_3$ and $V_2O_5$, respectively. In some embodiments, a digestible mixture of metal containing compounds having the correct stoichiometric ratio of one or more of Mo, V, Nb, and Bi could be used. Examples of such digestible mixtures include $(Mo,V)O_x$ and $BiNbO_x$. In one or more embodiments, the acid is selected from the group consisting of citric acid ($C_6H_8O_7$), oxalic acid ($C_2H_2O_4$), and mixtures thereof. In embodiments, the alkylene glycol is ethylene glycol.

The hydrothermal synthesis temperature is, in embodiments, from 150° C. to 250° C., from 160° C. to 250° C., from 170° C. to 250° C., from 180° C. to 250° C., from 190° C. to 250° C., from 200° C. to 250° C., from 210° C. to 250° C., from 220° C. to 250° C., from 230° C. to 250° C., from 240° C. to 250° C., from 150° C. to 240° C., from 160° C. to 240° C., from 170° C. to 240° C., from 180° C. to 240° C., from 190° C. to 240° C., from 200° C. to 240° C., from 210° C. to 240° C., from 220° C. to 240° C., from 230° C. to 240° C., from 150° C. to 230° C., from 160° C. to 230° C., from 170° C. to 230° C., from 180° C. to 230° C., from 190° C. to 230° C., from 200° C. to 230° C., from 210° C. to 230° C., from 220° C. to 230° C., from 150° C. to 220° C., from 160° C. to 220° C., from 170° C. to 220° C., from 180° C. to 220° C., from 190° C. to 220° C., from 200° C. to 220° C., from 210° C. to 220° C., from 150° C. to 210° C., from 160° C. to 210° C., from 170° C. to 210° C., from 180° C. to 210° C., from 190° C. to 210° C., from 200° C. to 210° C., from 150° C. to 200° C., from 160° C. to 200° C., from 170° C. to 200° C., from 180° C. to 200° C., from 190° C. to 200° C., from 150° C. to 190° C., from 160° C. to 190° C., from 170° C. to 190° C., from 180° C. to 190° C., from 150° C. to 180° C., from 160° C. to 180° C., from 170° C. to 180° C., from 150° C. to 170° C., from 160° C. to 170° C., or from 150° C. to 160° C.

In embodiments, the hydrothermal pressure is from 4 bar (400 kPa) to 40 bar (4000 kPa), such as from 5 bar (500 kPa) to 40 bar (4000 kPa), from 10 bar (1000 kPa) to 40 bar (4000 kPa), from 15 bar (1500 kPa) to 40 bar (4000 kPa), from 20 bar (2000 kPa) to 40 bar (4000 kPa), from 25 bar (2500 kPa) to 40 bar (4000 kPa), from 30 bar (3000 kPa) to 40 bar (4000 kPa), from 35 bar (3500 kPa) to 40 bar (4000 kPa), from 4 bar (400 kPa) to 35 bar (3500 kPa), from 5 bar (500 kPa) to 35 bar (3500 kPa), from 10 bar (1000 kPa) to 35 bar (3500 kPa), from 15 bar (1500 kPa) to 35 bar (3500 kPa), from 20 bar (2000 kPa) to 35 bar (3500 kPa), from 25 bar (2500 kPa) to 35 bar (3500 kPa), from 30 bar (3000 kPa) to 35 bar (3500 kPa), from 4 bar (400 kPa) to 30 bar (3000 kPa), from 5 bar (500 kPa) to 30 bar (3000 kPa), from 10 bar (1000 kPa) to 30 bar (3000 kPa), from 15 bar (1500 kPa) to 30 bar (3000 kPa), from 20 bar (2000 kPa) to 30 bar (3000 kPa), from 25 bar (2500 kPa) to 30 bar (3000 kPa), from 4 bar (400 kPa) to 25 bar (2500 kPa), from 5 bar (500 kPa) to 25 bar (2500 kPa), from 10 bar (1000 kPa) to 25 bar (2500 kPa), from 15 bar (1500 kPa) to 25 bar (2500 kPa), from 20 bar (2000 kPa) to 25 bar (2500 kPa), from 4 bar (400 kPa) to 20 bar (2000 kPa), from 5 bar (500 kPa) to 20 bar (2000 kPa), from 10 bar (1000 kPa) to 20 bar (2000 kPa), from 15 bar (1500 kPa) to 20 bar (2000 kPa), from 4 bar (400 kPa) to 15 bar (1500 kPa), from 5 bar (500 kPa) to 15 bar (1500 kPa), from 10 bar (1000 kPa) to 15 bar (1500 kPa), from 4 bar (400 kPa) to 10 bar (1000 kPa), or from 5 bar (500 kPa) to 10 bar (1000 kPa).

According to embodiments, after the $Mo_vV_wNb_yBi_zO_x$ oxidative dehydrogenation catalyst is separated from the retained liquids, the $Mo_bV_wNb_yBi_zO_x$ oxidative dehydrogenation catalyst is dried and optionally calcined by heating the dried $Mo_vV_wNb_yBi_zO_x$ oxidative dehydrogenation catalyst to a calcination temperature and holding the $Mo_vV_wNb_yBi_zO_x$ oxidative dehydrogenation catalyst at the calcination temperature for a period of time.

In embodiments, the $Mo_vV_wNb_yBi_zO_x$ oxidative dehydrogenation catalyst may be dried at any suitable temperature. However, to expedite drying, the $Mo_vV_wNb_yBi_zO_x$ oxidative dehydrogenation catalyst may, in embodiments, be dried at temperatures from 65° C. to 200° C., from 75° C. to 200° C., from 100° C. to 200° C., from 125° C. to 200° C., from 150° C. to 200° C., from 175° C. to 200° C., 65° C. to 175° C., from 75° C. to 175° C., from 100° C. to 175° C., from 125° C. to 175° C., from 150° C. to 175° C., 65° C. to 150° C., from 75° C. to 150° C., from 100° C. to 150° C., from 125° C. to 150° C., 65° C. to 125° C., from 75° C. to 125° C., from 100° C. to 125° C., 65° C. to 100° C., from 75° C. to 100° C., or 65° C. to 75° C.

In embodiments, the calcination takes place in an inert atmosphere, such as nitrogen ($N_2$), argon (Ar), or helium (He). In such embodiments, the calcination temperature is from 350° C. to 650° C., from 375° C. to 650° C., 400° C. to 650° C., from 425° C. to 650° C., from 450° C. to 650° C., from 475° C. to 650° C., from 500° C. to 650° C., from 525° C. to 650° C., from 550° C. to 650° C., from 575° C. to 650° C., from 600° C. to 650° C., from 625° C. to 650° C., from 350° C. to 625° C., from 375° C. to 625° C., from 400° C. to 625° C., from 425° C. to 625° C., from 450° C. to 625° C., from 475° C. to 625° C., from 500° C. to 625° C., from 525° C. to 625° C., from 550° C. to 625° C., from 575° C. to 625° C., from 600° C. to 625° C., from 350° C. to 600° C., from 375° C. to 600° C., from 400° C. to 600° C., from 425° C. to 600° C., from 450° C. to 600° C., from 475° C. to 600° C., from 500° C. to 600° C., from 525° C. to 600° C., from 550° C. to 600° C., from 575° C. to 600° C., from 350° C. to 575° C., from 375° C. to 575° C., from 400° C. to 575° C., from 425° C. to 575° C., from 450° C.

to 575° C., from 475° C. to 575° C., from 500° C. to 575° C., from 525° C. to 575° C., from 550° C. to 575° C., from 350° C. to 550° C., from 375° C. to 550° C., from 400° C. to 550° C., from 425° C. to 550° C., from 450° C. to 550° C., from 475° C. to 550° C., from 500° C. to 550° C., from 525° C. to 550° C., from 350° C. to 525° C., from 375° C. to 525° C., from 400° C. to 525° C., from 425° C. to 525° C., from 450° C. to 525° C., from 475° C. to 525° C., from 500° C. to 525° C., from 350° C. to 500° C., from 375° C. to 500° C., from 400° C. to 500° C., from 425° C. to 500° C., from 450° C. to 500° C., from 475° C. to 500° C., from 350° C. to 475° C., from 375° C. to 475° C., from 400° C. to 475° C., from 425° C. to 475° C., from 450° C. to 475° C., from 350° C. to 450° C., from 375° C. to 450° C., from 400° C. to 450° C., from 425° C. to 450° C., from 350° C. to 425° C., from 375° C. to 425° C., from 400° C. to 425° C. from 350° C. to 400° C., from 375° C. to 400° C., or from 350° C. to 375° C.

In embodiments, the calcination takes place in air. In such embodiments, the calcination temperature may be from 200° C. to 500° C., from 200° C. to 500° C., from 400° C. to 500° C., from 425° C. to 500° C., from 450° C. to 500° C., from 475° C. to 500° C., from 350° C. to 475° C., from 375° C. to 475° C., from 400° C. to 475° C., from 425° C. to 475° C., from 450° C. to 475° C., from 350° C. to 450° C., from 375° C. to 450° C., from 400° C. to 450° C., from 425° C. to 450° C., from 350° C. to 425° C., from 375° C. to 425° C., from 400° C. to 425° C. from 350° C. to 400° C., from 375° C. to 400° C., or from 350° C. to 375° C.

After the $Mo_vV_wNb_yBi_zO_x$ oxidative dehydrogenation catalyst has been formed, the $Mo_vV_wNb_yBi_zO_x$ oxidative dehydrogenation catalyst may be used in processes for converting alkanes in an alkane-containing feed stream to olefins. The processes disclosed and described herein may provide improved olefin selectivity by the $Mo_vV_wNb_yBi_zO_x$ oxidative dehydrogenation catalyst as time on stream increases. Processes disclosed and described herein generally include contacting a feed stream comprising alkanes (paraffins) with the $Mo_vV_wNb_yBi_zO_x$ oxidative dehydrogenation catalyst in a reaction zone, converting at least a portion of the alkanes to olefins yielding a product stream comprising paraffins and olefins. The reaction zone is not particularly limited and any type of reactor allowing for cyclic or continuous operation of the process may be used in embodiments. In embodiments, the reaction zone can be a fixed bed reactor, a fluidized bed reactor, a moving bed reactor, a bubbling bed reactor, circulating fluidized reactor, reverse flow reactor, or an ebullated bed reactor (each optionally with an oxygen co-feed). The reaction zone is not particularly limited to a single reaction zone and can consist of multiple reactors in either series or parallel configuration. Finally, the paraffins and olefins in the product stream are separated, the paraffins may be recycled back to the feed stream, and the olefins are used in downstream systems or as materials in various products and processes. Processes according to embodiments disclosed and described herein will be provided in more detail below.

According to embodiments, a feed stream is fed into a reaction zone, the feed stream comprises at least one alkane. In embodiments, the feed stream may be comprised entirely of alkane (e.g., 100% alkane). In one or more embodiments, the feed stream may contain oxygen, steam and/or inert gas. In embodiments, the feed stream comprises from 30 volume percent (vol %) to 90 vol % alkane, from 35 vol % to 90 vol % alkane, from 40 vol % to 90 vol % alkane, from 45 vol % to 90 vol % alkane, from 50 vol % to 90 vol % alkane, from 55 vol % to 90 vol % alkane, from 60 vol % to 90 vol % alkane, from 65 vol % to 90 vol % alkane, from 70 vol % to 90 vol % alkane, from 75 vol % to 90 vol % alkane, from 80 vol % to 90 vol % alkane, from 85 vol % to 90 vol % alkane, from 30 volume percent (vol %) to 85 vol % alkane, from 35 vol % to 85 vol % alkane, from 40 vol % to 85 vol % alkane, from 45 vol % to 85 vol % alkane, from 50 vol % to 85 vol % alkane, from 55 vol % to 85 vol % alkane, from 60 vol % to 85 vol % alkane, from 65 vol % to 85 vol % alkane, from 70 vol % to 85 vol % alkane, from 75 vol % to 85 vol % alkane, from 80 vol % to 85 vol % alkane, from 30 volume percent (vol %) to 80 vol % alkane, from 35 vol % to 80 vol % alkane, from 40 vol % to 80 vol % alkane, from 45 vol % to 80 vol % alkane, from 50 vol % to 80 vol % alkane, from 55 vol % to 80 vol % alkane, from 60 vol % to 80 vol % alkane, from 65 vol % to 80 vol % alkane, from 70 vol % to 80 vol % alkane, from 75 vol % to 80 vol % alkane, from 30 volume percent (vol %) to 75 vol % alkane, from 35 vol % to 75 vol % alkane, from 40 vol % to 75 vol % alkane, from 45 vol % to 75 vol % alkane, from 50 vol % to 75 vol % alkane, from 55 vol % to 75 vol % alkane, from 60 vol % to 75 vol % alkane, from 65 vol % to 75 vol % alkane, from 70 vol % to 75 vol % alkane, from 30 volume percent (vol %) to 70 vol % alkane, from 35 vol % to 70 vol % alkane, from 40 vol % to 70 vol % alkane, from 45 vol % to 70 vol % alkane, from 50 vol % to 70 vol % alkane, from 55 vol % to 70 vol % alkane, from 60 vol % to 70 vol % alkane, from 65 vol % to 70 vol % alkane, from 30 volume percent (vol %) to 65 vol % alkane, from 35 vol % to 65 vol % alkane, from 40 vol % to 65 vol % alkane, from 45 vol % to 65 vol % alkane, from 50 vol % to 65 vol % alkane, from 55 vol % to 65 vol % alkane, from 60 vol % to 65 vol % alkane, from 30 volume percent (vol %) to 60 vol % alkane, from 35 vol % to 60 vol % alkane, from 40 vol % to 60 vol % alkane, from 45 vol % to 60 vol % alkane, from 50 vol % to 60 vol % alkane, from 55 vol % to 60 vol % alkane, from 30 volume percent (vol %) to 55 vol % alkane, from 35 vol % to 55 vol % alkane, from 40 vol % to 55 vol % alkane, from 45 vol % to 55 vol % alkane, from 50 vol % to 55 vol % alkane, from 30 volume percent (vol %) to 50 vol % alkane, from 35 vol % to 50 vol % alkane, from 40 vol % to 50 vol % alkane, from 45 vol % to 50 vol % alkane, from 30 volume percent (vol %) to 45 vol % alkane, from 35 vol % to 45 vol % alkane, from 40 vol % to 45 vol % alkane, from 30 volume percent (vol %) to 40 vol % alkane, from 35 vol % to 40 vol % alkane, or from 30 volume percent (vol %) to 35 vol % alkane.

In embodiments, the at least one alkane is selected from the group consisting of ethane, propane, and combinations thereof. In embodiments, the inert gas is selected from the group consisting of nitrogen, $CO_2$, and combination thereof.

According to one or more embodiments, the weight ratio of the $Mo_vV_wNb_yBi_zO_x$ oxidative dehydrogenation catalyst in the reaction zone to alkane in the reaction zone is from 250 to 10, from 225 to 10, from 200 to 10, from 175 to 10, from 150 to 10, from 125 to 10, from 100 to 10, from 75 to 10, from 50 to 10, from 25 to 10, from 250 to 25, from 225 to 25, from 200 to 25, from 175 to 25, from 150 to 25, from 125 to 25, from 100 to 25, from 75 to 25, from 50 to 25, from 250 to 50, from 225 to 50, from 200 to 50, from 175 to 50, from 150 to 50, from 125 to 50, from 100 to 50, from 75 to 50, from 250 to 75, from 225 to 75, from 200 to 75, from 175 to 75, from 150 to 75, from 125 to 75, from 100 to 75, from 250 to 100, from 225 to 100, from 200 to 100, from 175 to 100, from 150 to 100, from 125 to 100, from 250 to 125, from 225 to 125, from 200 to 125, from 175 to 125, from 150 to 125, from 250 to 150, from 225 to 150, from 200 to 150, from 175 to 150, from 250 to 175, from 225 to 175, from 200 to 175, from 250 to 200, from 225 to 200, or from 250 to 225. In embodiments where the reaction zone in a fluidized bed catalyst or the like, the catalyst to alkane ratio is controlled by the mass feed rate of alkane and the mass feed rate of catalyst to the reaction zone.

In embodiments, the feed stream is essentially free from oxygen, meaning that the feed stream comprises less than 2.0 volume percent (vol %) oxygen, less than 1.5 vol % oxygen, or less than 0.5 vol % oxygen. In one or more embodiments, the feed stream is free of oxygen.

In one or more embodiments, an oxygen stream is added to the reaction zone. The concentration of oxygen in the oxygen stream is not particularly limited. For example, the oxygen concentration in the oxygen stream may be from 0.1 vol % to 99.9 vol %, such as from 5.0 vol % to 95.0 vol %, from 10.0 vol % to 90.0 vol %, from 15.0 vol % to 85.0 vol %, from 20.0 vol % to 80.0 vol %, from 25.0 vol % to 75.0 vol %, from 30.0 vol % to 70.0 vol %, from 35.0 vol % to 65.0 vol %, from 40.0 vol % to 60.0 vol %, or from 45.0 vol % to 55.0 vol %. In one or more embodiments, the concentration of oxygen in the oxygen stream is relatively low, such as from 0.1 vol % to 5.0 vol %, from 0.2 vol % to 5.0 vol %, from 0.5 vol % to 5.0 vol %, from 0.8 vol % to 5.0 vol %, from 1.0 vol % to 5.0 vol %, from 1.2 vol % to 5.0 vol %, from 1.5 vol % to 5.0 vol %, from 1.8 vol % to 5.0 vol %, from 2.0 vol % to 5.0 vol %, from 2.2 vol % to 5.0 vol %, from 2.5 vol % to 5.0 vol %, from 2.8 vol % to 5.0 vol %, from 3.0 vol % to 5.0 vol %, from 3.2 vol % to 5.0 vol %, from 3.5 vol % to 5.0 vol %, from 3.8 vol % to 5.0 vol %, from 4.0 vol % to 5.0 vol %, from 4.2 vol % to 5.0 vol %, from 4.5 vol % to 5.0 vol %, or from 4.8 vol % to 5.0 vol %. In embodiments, the oxygen stream may be air, which generally has an oxygen concentration of about 21.0 vol %.

The oxygen stream may, in embodiments, be added to the reaction zone sequentially to the feed stream, such that the feed stream and the oxygen stream are not added to the reaction zone at the same time. It should be understood that in embodiments, the oxygen stream may be added at various points within the reaction process. This may be accomplished by introducing the oxygen stream into the reaction zone at different locations within the reaction zone and/or introducing the oxygen stream at different time periods while the reaction is taking place.

In one or more embodiments, the oxygen stream is added to the reaction zone simultaneously to the feed stream. In such embodiments, the volume ratio of oxygen (in the oxygen stream) to alkanes (in the feed stream) in the reaction zone is from greater than 0.0 to 3.0, from 0.5 to 3.0, from 1.0 to 3.0, from 1.5 to 3.0, from 2.0 to 3.0, from 2.5 to 3.0, from greater than 0.0 to 2.5, from 0.5 to 2.5, from 1.0 to 2.5, from 1.5 to 2.5, from 2.0 to 2.5, from greater than 0.0 to 2.0, from 0.5 to 2.0, from 1.0 to 2.0, from 1.5 to 2.0, from greater than 0.0 to 1.5, from 0.5 to 1.5, from 1.0 to 1.5, from greater than 0.0 to 1.0, from 0.5 to 1.0, or from greater than 0.0 to 0.5.

The feed stream is contacted with the $Mo_vV_wNb_yBi_zO_x$ oxidative dehydrogenation catalyst as disclosed and described herein in the reaction zone under reaction conditions sufficient to form a product stream comprising olefins. The reaction conditions comprise a temperature within the reaction zone ranging, according to one or more embodiments, the temperature within the reaction zone is from 300° C. to 700° C., from 350° C. to 700° C., from 400° C. to 700° C., from 450° C. to 700° C., from 500° C. to 700° C., from 550° C. to 700° C., from 600° C. to 700° C., from 650° C. to 700° C., from 300° C. to 650° C., from 350° C. to 650° C., from 400° C. to 650° C., from 450° C. to 650° C., from 500° C. to 650° C., from 550° C. to 650° C., from 600° C. to 600° C., from 300° C. to 600° C., from 350° C. to 600° C., from 400° C. to 600° C., from 450° C. to 600° C., from 500° C. to 600° C., from 550° C. to 600° C., from 300° C. to 550° C., from 350° C. to 550° C., from 400° C. to 550° C., from 450° C. to 550° C., from 500° C. to 550° C., from 300° C. to 500° C., from 350° C. to 500° C., from 400° C. to 500° C., from 450° C. to 500° C., from 300° C. to 450° C., from 350° C. to 450° C., from 400° C. to 450° C., from 300° C. to 400° C., from 350° C. to 400° C., or from 300° C. to 350° C.

The reaction conditions also, in embodiments, include a pressure inside the reaction zone from 0 barg (0 KPa) to 20 barg (2000 KPa), from 5 barg (500 KPa) to 20 barg (2000 KPa), from 10 barg (1000 KPa) to 20 barg (2000 KPa), from 15 barg (1500 KPa) to 20 barg (2000 KPa), from 0 barg (0 KPa) to 15 barg (1500 KPa), form 5 barg (500 KPa) to 15 barg (1500 KPa), from 10 barg (1000 KPa) to 15 barg (1500 KPa), from 0 barg (0 KPa) to 10 barg (1000 KPa), form 5 barg (500 KPa) to 10 barg (1000 KPa), or from 0 barg (0 KPa) to 5 barg (500 KPa).

According to embodiments, the weight hour space velocity (WHSV) of the alkane feed stream and, optionally, the oxygen stream within the reaction zone is from 0.1 per hour (/h) to 10.0/h, from 0.5/h to 10.0/h, from 1.0/h to 10.0/h, from 2.0/h to 10.0/h, from 3.0/h to 10.0/h, from 4.0/h to 10.0/h, from 5.0/h to 10.0/h, from 6.0/h to 10.0/h, from 7.0/h to 10.0/h, from 8.0/h to 10.0/h, from 9.0/h to 10.0/h, 0.1/h to 9.0/h, from 0.5/h to 9.0/h, from 1.0/h to 9.0/h, from 2.0/h to 9.0/h, from 3.0/h to 9.0/h, from 4.0/h to 9.0/h, from 5.0/h to 9.0/h, from 6.0/h to 9.0/h, from 7.0/h to 9.0/h, from 8.0/h to 9.0/h, 0.1/h to 8.0/h, from 0.5/h to 8.0/h, from 1.0/h to 8.0/h, from 2.0/h to 8.0/h, from 3.0/h to 8.0/h, from 4.0/h to 8.0/h, from 5.0/h to 8.0/h, from 6.0/h to 8.0/h, from 7.0/h to 8.0/h, 0.1/h to 7.0/h, from 0.5/h to 7.0/h, from 1.0/h to 7.0/h, from 2.0/h to 7.0/h, from 3.0/h to 7.0/h, from 4.0/h to 7.0/h, from 5.0/h to 7.0/h, from 6.0/h to 7.0/h, 0.1/h to 6.0/h, from 0.5/h to 6.0/h, from 1.0/h to 6.0/h, from 2.0/h to 6.0/h, from 3.0/h to 6.0/h, from 4.0/h to 6.0/h, from 5.0/h to 6.0/h, 0.1/h to 5.0/h, from 0.5/h to 5.0/h, from 1.0/h to 5.0/h, from 2.0/h to 5.0/h, from 3.0/h to 5.0/h, from 4.0/h to 5.0/h, 0.1/h to 4.0/h, from 0.5/h to 4.0/h, from 1.0/h to 4.0/h, from 2.0/h to 4.0/h, from 3.0/h to 4.0/h, 0.1/h to 3.0/h, from 0.5/h to 3.0/h, from 1.0/h to 3.0/h, from 2.0/h to 3.0/h, 0.1/h to 2.0/h, from 0.5/h to 2.0/h, from 1.0/h to 2.0/h, 0.1/h to 1.0/h, from 0.5/h to 1.0/h, or 0.1/h to 0.5/h.

EXAMPLES

Example 1

A mixture of 34 mL of $H_2O$ and 80 microliters of ethylene glycol was added to a 45 mL Teflon-insert autoclave (Model 4744 General Purpose Acid Digestion Vessel, Parr). While stirring the above mixture, 2.7126 g of $MoO_3$, 0.5141 g of $V_2O_5$, 0.4373 g of $Bi_2O_3$, 0.286 g of $Nb_2O_5 \cdot xH_2O$, 0.2711 g of Citric acid and 0.2388 g of oxalic acid were added sequentially and stirred for 10 minutes. Hydrothermal synthesis of $MoV_{0.3}Nb_{0.1}Bi_{0.1}O_x$ was performed in a rotating shaft oven at 180° C. for 48 hours while rotating at 10 rpm. The obtained material from the hydrothermal synthesis was purified with 90 mL of deionized water using vacuum filtration. The sample was subsequently dried at 85° C. overnight.

After drying, the material was calcined at 450° C. (at a heating rate of 2° C./min) under a flow of $N_2$, for 2 hours. The material was compacted under 7-ton pressure and crushed and sieved to 40-80 mesh prior to loading in the reactor. Reaction conditions will be discussed in detail below.

Example 2

A mixture of 34 mL of $H_2O$ and 160 microliters of ethylene glycol was added to a 45 mL Teflon-insert autoclave (Model 4744 General Purpose Acid Digestion Vessel, Parr). While stirring the mixture, 2.7126 g of $MoO_3$, 0.5141 g of $V_2O_5$, 0.4373 g of $Bi_2O_3$, 0.286 g of $Nb_2O_5 \cdot xH_2O$, 0.5422 g of Citric acid and 0.2388 g of oxalic acid were added sequentially and stirred for 10 min. Hydrothermal synthesis of $MoV_{0.3}Nb_{0.1}Bi_{0.1}O_x$ was performed in a rotating shaft oven at 190° C. for 48 hours while rotating at 10 rpm. The obtained material from the hydrothermal synthesis was purified with 90 mL of deionized water using vacuum filtration. The material was subsequently dried at 85° C. overnight.

After drying, the material was calcined at 450° C. (at a heating rate of 2° C./min) under a flow of $N_2$, for 2 hours. The material was compacted under 7-ton pressure and crushed and sieved to 40-80 mesh prior to loading in the reactor. Reaction conditions will be discussed in detail below.

Example 3

A mixture of 34 mL of $H_2O$ and 80 microliters of ethylene glycol was added to a 45 mL Teflon-insert autoclave (Model 4744 General Purpose Acid Digestion Vessel, Parr). While stirring the mixture, 2.7126 g of $MoO_3$, 0.5141 g of $V_2O_5$, 0.4373 g of $Bi_2O_3$, 0.8416 g of $(NH_4)Nb(C_2O_4)_2 \cdot xH_2O$ and 0.2711 g of Citric acid were added sequentially and stirred for 10 min. Hydrothermal synthesis of $MoV_{0.3}Nb_{0.1}Bi_{0.1}$ was performed in a rotating shaft oven at 190° C. for 48 hours while rotating at 10 rpm. The obtained material from the hydrothermal synthesis was purified with 90 mL of deionized water using vacuum filtration. The material was subsequently dried at 85° C. overnight.

After drying, the material was calcined at 450° C. (at a heating rate of 2° C./min) under a flow of $N_2$, for 2 hours. The material was compacted under 7-ton pressure and crushed and sieved to 40-80 mesh prior to loading in the reactor. Reaction conditions will be discussed in detail below.

Comparative Example 1

A mixture of 34 mL of $H_2O$ and 80 microliters of ethylene glycol was added to a 45 mL Teflon-insert autoclave (Model 4744 General Purpose Acid Digestion Vessel, Parr). While stirring the mixture, 2.7126 g of $MoO_3$, 0.5141 g of $V_2O_5$, 0.2186 g of $Bi_2O_3$, 0.2711 g of Citric acid and 0.1194 g of oxalic acid were added sequentially and stirred for 10 min. Hydrothermal synthesis of $MoV_{0.3}Bi_{0.05}$ was performed in a rotating shaft oven at 190° C. for 48 hours while rotating at 10 rpm. The obtained material from the hydrothermal synthesis was purified with 90 mL of deionized water using vacuum filtration. The material was subsequently dried at 85° C. overnight.

After drying, the material was calcined at 450° C. (at a heating rate of 2° C./min) under a flow of $N_2$, for 2 hours. The material was compacted under 7-ton pressure and crushed and sieved to 40-80 mesh prior to loading in the reactor. Reaction conditions will be discussed in detail below.

Comparative Example 2

A mixture of 34 mL of $H_2O$ and 80 microliter of ethylene glycol was added to a 45 mL Teflon-insert autoclave (Model 4744 General Purpose Acid Digestion Vessel, Parr). While stirring the mixture, 2.7126 g of $MoO_3$, 0.5141 g of $V_2O_5$, 0.3033 g of $Sb_2O_5$, 0.8416 g of $(NH_4)Nb(C_2O_4)_2 \cdot xH_2O$ and 0.2711 g of Citric acid were added sequentially and stirred for 10 min. Hydrothermal synthesis of $MoV_{0.3}Nb_{0.1}Sb_{0.1}O_x$ was performed in a rotating shaft oven at 190° C. for 48 hours while rotating at 10 rpm. The obtained material from the hydrothermal synthesis was purified with 90 mL of deionized water using vacuum filtration. The material was subsequently dried at 85° C. overnight.

After drying, the material was calcined at 450° C. (at a heating rate of 2° C./min) under a flow of $N_2$, for 2 hours. The material was compacted under 7-ton pressure and crushed and sieved to 40-80 mesh prior to loading in the reactor. Reaction conditions will be discussed in detail below.

Comparative Example 3

A mixture of 34 mL of $H_2O$ and 80 microliter of ethylene glycol was added to a 45 mL Teflon-insert autoclave (Model 4744 General Purpose Acid Digestion Vessel, Parr). While stirring the mixture, 2.7126 g of $MoO_3$, 0.5141 g of $V_2O_5$, 0.4373 g of $Bi_2O_3$, 0.2711 g of Citric acid and 0.2382 g of oxalic acid were added sequentially and stirred for 10 min. Hydrothermal synthesis of $MoV_{0.3}Bi_{0.1}$ was performed in a rotating shaft oven at 190° C. for 48 hours while rotating at 10 rpm. The obtained material from the hydrothermal synthesis was purified with 90 mL of deionized water using vacuum filtration. The material was subsequently dried at 85° C. overnight.

After drying, the material was calcined at 450° C. (at a heating rate of 2° C./min) under a flow of $N_2$, for 2 hours. The obtained material did not show any material with Pba2-32 crystal structure, and predominantly consisted of unreacted $MoO_3$. Therefore, this material was not tested in the reactor testing below.

Reactor Testing

Performance testing was performed in a fixed-bed reactor set-up from Sintef (High Pressure Reactor Assembly Module), with SS316 reactor tubes (I.D. 3 mm). For catalytic testing, 250 mg of 40-80 mesh catalyst particles were loaded in the reactors, and the reactors were operated in cyclic mode in which periods of ethane exposure were alternated with inert gas purge and oxidative regeneration at the desired temperature:

A LODh step used a 20 mL/min flow of 50 vol. % Ethane in He at a pressure of 2.5 bar (absolute) and a WHSV of 3.2/hr.

A regeneration step used a 10 mL/min flow of 2.5 vol. % $O_2$ in $N_2$ at a pressure of 2.5 bar (absolute).

The reactor effluent composition was obtained by gas chromatography (GC) and the conversion and carbon-based selectivities are calculated using the following equations:

$$XC_2H_6(\%) = [(\eta C_2H_6, \text{in} - \eta C_2H_6, \text{out}) / \eta C_2H_6, \text{in}] \cdot 100; \quad (1)$$

and $$S_j(\%) = \left[\alpha j \cdot \eta j, \text{out} \middle/ \sum \alpha j \cdot \eta j, \text{out}\right] \cdot 100 \quad (2)$$

where $XC_2H_6$ is defined as the $C_2H_6$ conversion (%), η, in is defined as the molar inlet flow of the component (mol/min), η, out is the molar outlet flow of the component (mol/min), $S_j$ is defined as the carbon based selectivity to product j (%), αj is the number of carbon atoms for product j. Carbon balance for all experiments was within 99-102% for all experiments.

The catalyst/ethane ratio (g/g) is calculated based on the time-on-stream (TOS, min) in which the GC analyzes the reactor effluent:

$$Cat/\text{ethane} = w/(TOS \cdot \eta C_2H_6,\ \text{in} \cdot MW_{C2H6}) \quad (3)$$

Where w is defined as the catalyst mass, $\eta C_2H_6$, in is the molar inlet flow of ethane (mol/min) and $MW_{C2H6}$ is the molecular weight of ethane (30 g/mol).

The results of the catalytic testing at 450° C. are shown in Table 2 below.

TABLE 2

Catalytic Performance of selected examples in anaerobic lattice oxidative dehydrogenation of Ethane at 450° C.

| | Cycle | $XC_2H_6$ (%) | $SC_2H_4$ (%) | SCO (%) | $SCO_2$ (%) | $SCH_4$ (%) | Cat/ Ethane |
|---|---|---|---|---|---|---|---|
| Example 1 | 2-5 | 20.7 | 71.0 | 14.1 | 14.7 | 0.2 | 110 |
| | 10-15 | 24.0 | 81.7 | 9.8 | 8.5 | <0.1 | 110 |
| | 20-25 | 22.9 | 84.9 | 8.3 | 6.8 | <0.1 | 110 |
| | 30-35 | 20.5 | 85.6 | 7.9 | 6.5 | <0.1 | 110 |
| Example 2 | 2-5 | 24 | 86.5 | 7.4 | 6.1 | <0.1 | 95 |
| | 10-15 | 26.2 | 87.6 | 6.9 | 5.5 | <0.1 | 95 |
| | 20-25 | 27.6 | 87.8 | 6.8 | 5.4 | <0.1 | 95 |
| Example 3 | 2-5 | 13.3 | 70.1 | 16.8 | 12.2 | <0.1 | 77 |
| | 10-15 | 11.5 | 73.3 | 15.9 | 10.8 | <0.1 | 77 |
| | 20-25 | 10.4 | 75.4 | 14.9 | 9.7 | <0.1 | 77 |
| | 30-35 | 11 | 76.1 | 14.5 | 9.4 | 0 | 77 |
| Comp. Ex. 1 | 3-5 | 16.5 | 81.3 | 11.0 | 7.7 | <0.1 | 88 |
| | 10-15 | 10.1 | 80.7 | 13.3 | 6.0 | 0 | 88 |
| | 20-25 | 6.5 | 78.1 | 15.8 | 6.1 | 0 | 88 |
| | 30-35 | 4.3 | 76.0 | 17.8 | 6.2 | 0 | 88 |
| Comp Ex. 2 | 2-5 | 15.5 | 64.7 | 17.4 | 17.9 | <0.1 | 78 |
| | 10-15 | 17.4 | 67 | 19.2 | 13.8 | <0.1 | 78 |
| | 20-25 | 17.4 | 68.5 | 19.4 | 12.1 | <0.1 | 78 |

As can be observed from Table 2, Examples 1 to 3 demonstrate high stability with respect to catalyst activity, as well as a slow increase in ethylene selectivity as function of cumulative redox cycles. This highlights the excellent performance of Bi-containing materials which crystallize in the Pba2-32 crystal structures.

In contrast, Comparative Example 1 demonstrates high initial activity and selectivity, but the performance of this material rapidly degrades as function of cumulative redox cycles. This highlights the importance of Nb presence in the material.

Comparative Example 2 demonstrates either lower activity and/or selectivity compared to the inventive examples. This highlights the excellent performance of Bi-containing materials which crystallize in Pba2-32 structures.

It will be apparent to those skilled in the art that various modifications and variations can be made to the embodiments described herein without departing from the spirit and scope of the claimed subject matter. Thus, it is intended that the specification cover the modifications and variations of the various embodiments described herein provided such modification and variations come within the scope of the appended claims and their equivalents.

Additional performance testing with oxygen co-feed (aerobic) was performed in a fixed-bed reactor set-up, with a ceramic-lined Incoloy reactor (ID. 4 mm) For catalytic testing, 210 mg of 40-80 mesh catalyst particles were loaded in the reactor, and the reactor was operated in cyclic mode in which periods of ethane and oxygen exposure were alternated with oxidative regeneration at the desired temperature.

An oxidative dehydrogenation step used a 95 mL/min flow of 10 vol. % Ethane and 5 vol. % Oxygen in He at a pressure of 1.4 bar (absolute) and a WHSV of 3.2/hr.

A regeneration step used a 45 mL/min flow of air (21 vol. % $O_2$) at a pressure of 1.4 bar (absolute).

Since molecular oxygen is present in the feed to replenish lattice oxygen, time-on-stream is shown in place of Cat/Ethane ratio.

The results of the catalytic testing at 450° C. are shown in Table below.

TABLE 3

Catalytic Performance of selected example in aerobic oxidative dehydrogenation of Ethane at 450° C.

| | Cycle | $XC_2H_6$ (%) | $SC_2H_4$ (%) | SCO (%) | $SCO_2$ (%) | $SC_2H_2$ (%) | TOS (sec) |
|---|---|---|---|---|---|---|---|
| Example 2 | 31-35 | 50.6 | 84.0 | 12.1 | 3.7 | <0.2 | 11 |
| | 51-55 | 52.1 | 83.7 | 12.6 | 3.5 | <0.2 | 240 |

As can be observed from Table 3, Example 2 can be used as an oxidative dehydrogenation catalyst with high stability. Under aerobic condition, the catalyst activity is sustained over longer periods of time and is about 2× higher with comparative selectivity to the anaerobic lattice oxygen dehydrogenation in Table 2.

The invention claimed is:

1. An oxidative dehydrogenation catalyst comprising:

a structure comprising a mixed oxide of molybdenum (Mo), vanadium (V), niobium (Nb), and bismuth (Bi) having a formula $Mo_vV_wNb_yBi_zO_x$, wherein v is 1, w is from 0.1 to 0.5, y is from 0.001 to 0.3, z is from 0.01 to 0.3, and x is an oxygen content required to charge-balance the structure, the oxidative dehydrogenation catalyst has a crystallographic structure with the Pba2-32 space group, characterized by reflections determined with Cu—$K_\alpha$ X-ray diffraction (XRD) as follows:

| 2θ (±0.3°) | Rel. Intensity (%) |
|---|---|
| 5.3 | 0.2-8 |
| 6.6 | 1.5-15 |
| 7.84 | 2.5-45 |
| 8.95 | 4-21 |
| 22.17 | 100 |
| 27.2 | 20-50 |
| 28.1 | 10-30. |

2. The oxidative dehydrogenation catalyst of claim 1, wherein the oxidative dehydrogenation catalyst consists of the structure comprising oxides of molybdenum (Mo), vanadium (V), niobium (Nb), and bismuth (Bi) having a formula $Mo_vV_wNb_yBi_zO_x$, wherein v is 1, w is from 0.1 to 0.5, y is from 0.001 to 0.3, z is from 0.01 to 0.3, and x is the oxygen content required to charge-balance the structure.

3. The oxidative dehydrogenation catalyst of claim 1, wherein the oxidative dehydrogenation catalyst is essentially free of tellurium (Te).

4. The oxidative dehydrogenation catalyst of claim 1, wherein the oxidative dehydrogenation catalyst has the following formula: $MoV_{0.2-0.3}Nb_{0.1}Bi_{0.1}O_x$.

5. A method for forming an oxidative dehydrogenation catalyst, the method comprising:

adding a molybdenum-containing compound, a vanadium-containing compound, a bismuth-containing compound, a niobium-containing compound, and one or more organic acids to a mixture of alkylene glycol or alcohol amine and water to form a starting mixture;

treating the starting mixture by hydrothermal synthesis at a hydrothermal synthesis temperature that is from 180° C. to 220° C.;

separating $Mo_vV_wNb_yBi_zO_x$ from retained liquids, and calcining the $Mo_vV_wNb_yBi_zO_x$ in an inert atmosphere, wherein the starting mixture comprises at least one of molybdenum trioxide ($MoO_3$) and vanadium pentoxide ($V_2O_5$).

6. The method for forming an oxidative dehydrogenation catalyst of claim 5, wherein the one or more organic acids comprises at least one of citric acid ($C_6H_8O_7$), oxalic acid ($C_2H_2O_4$), and mixtures thereof.

7. The method for forming an oxidative dehydrogenation catalyst of claim 5, wherein the niobium-containing compound is selected from the group consisting of niobium oxide, niobic acid ($Nb_2O_5 \cdot xH_2O$), ammonium niobium oxalate ($(NH_4)Nb(C_2O_4)_2xH_2O$), niobium ethoxide, and mixtures thereof.

8. The method for forming an oxidative dehydrogenation catalyst of claim 5, wherein the bismuth-containing compound is selected from the group consisting of bismuth oxide ($Bi_2O_3$), bismuth sulfate ($Bi_2(SO_4)_3$), bismuth citrate ($BiC_6H_5O_7$), and bismuth nitrate ($Bi(NO_3)_3$).

9. The method for forming an oxidative dehydrogenation catalyst of claim 5, wherein the alkylene glycol is ethylene glycol ($C_2H_6O_2$).

10. The method for forming an oxidative dehydrogenation catalyst of claim 5, wherein the hydrothermal synthesis temperature is from 180° C. to 210° C.

11. The method for forming an oxidative dehydrogenation catalyst of claim 5, wherein the starting mixture comprises $MoO_3$ and $V_2O_5$.

12. A method for converting paraffins to olefins, the method comprising:

contacting a feed stream comprising paraffins with the oxidative dehydrogenation catalyst of claim 1;

converting at least a portion of the paraffins to olefins, thereby yielding a product stream comprising paraffins and olefins; and separating the olefins from the paraffins in the product stream.

13. The method of claim 12, wherein the method further comprises contacting a second stream comprising oxygen with the feed stream comprising paraffins and the oxidative dehydrogenation catalyst.

14. The method of claim 13, wherein the conversion occurs at a temperature that is from 300° C. to 700° C., and a pressure that is from 0 barg to 20 barg.

15. The method of claim 13, wherein the conversion occurs at an alkane weight hourly space velocity (WHSV) that is from 0.1/hr to 10/hr.

* * * * *